US00PP24859P2

(12) United States Plant Patent
Kobayashi

(10) Patent No.: US PP24,859 P2
(45) Date of Patent: Sep. 9, 2014

(54) POINSETTIA PLANT NAMED 'PER1910'

(50) Latin Name: ***Euphorbia pulcherrima* Willd.**
Varietal Denomination: PER1910

(71) Applicant: Ruth Kobayashi, Carlsbad, CA (US)

(72) Inventor: Ruth Kobayashi, Carlsbad, CA (US)

(73) Assignee: Ecke Ranch B.V., De lier (NL)

( * ) Notice: Subject to any disclaimer, the term of this patent is extended or adjusted under 35 U.S.C. 154(b) by 3 days.

(21) Appl. No.: 13/694,957

(22) Filed: Jan. 22, 2013

(51) Int. Cl.
*A01H 5/00* (2006.01)

(52) U.S. Cl.
USPC ..... Plt./303

(58) Field of Classification Search
USPC ..... Plt./303
See application file for complete search history.

*Primary Examiner* — Anne Grunberg
(74) *Attorney, Agent, or Firm* — C. A. Whealy

(57) ABSTRACT

A new and distinct cultivar of Poinsettia plant named 'PER1910', characterized by its uniform, upright and mounded plant habit; moderately vigorous growth habit; freely and upright branching habit; dark greyed green-colored leaves; mid-season flowering response; large inflorescences with marbled pale yellow and dark pink-colored flower bracts; and good post-production longevity.

1 Drawing Sheet

Botanical designation: *Euphorbia pulcherrima* Willd.
Cultivar denomination: 'PER1910'.

BACKGROUND OF THE INVENTION

The present invention relates to a new and distinct cultivar of Poinsettia plant, botanically known as *Euphorbia pulcherrima* Willd., and hereinafter referred to by the name 'PER1910'.

The new Poinsettia plant is a product of a planned breeding program conducted by the Inventor in Encinitas, Calif. The objective of the breeding program is to create new uniform Poinsettia plants having large inflorescences with attractive flower bracts and excellent post-production longevity.

The new Poinsettia plant originated is a naturally-occurring whole plant mutation of *Euphorbia pulcherrima* Willd. 'PER1139', disclosed in U.S. Plant Pat. No. 22,180. The new Poinsettia plant was discovered and selected by the Inventor as a single flowering plant from within a population of plants of 'PER1139' in a controlled greenhouse environment in Encinitas, Calif. on Sep. 22, 2009.

Asexual reproduction of the new Poinsettia plant by terminal vegetative cuttings in a controlled greenhouse environment in Encinitas, Calif. since January, 2010 has shown that the unique features of this new Poinsettia plant are stable and reproduced true to type in successive generations of asexual reproduction.

SUMMARY OF THE INVENTION

Plants of the new Poinsettia have not been observed under all possible environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'PER1910'. These characteristics in combination distinguish 'PER1910' as a new and distinct Poinsettia plant:

1. Uniform, upright and mounded plant habit.
2. Moderately vigorous growth habit.
3. Freely and upright branching habit.
4. Dark greyed green-colored leaves.
5. Mid-season flowering response; under natural season conditions, plants flower in late November in Southern California.
6. Large inflorescences with marbled pale yellow and dark pink-colored flower bracts.
7. Good post-production longevity.

In side-by-side comparisons conducted in Encinitas, Calif., plants of the new Poinsettia differ primarily from plants of the parent, 'PER1139', in flower bract color as plants of 'PER1139' have dark red-colored flower bracts. In addition, plants of the new Poinsettia and 'PER1139' differ slightly in leaf color.

Plants of the new Poinsettia can be compared to plants of the *Euphorbia pulcherrima* Willd. 'Peterstar Pink', disclosed in U.S. Plant Pat. No. 9,879. In side-by-side comparisons conducted in Encinitas, Calif., plants of the new Poinsettia differed primarily from plants of 'Peterstar Pink' in the following characteristics:

1. Branching habit of plants of the new Poinsettia was more upright than branching habit of plants of 'Peterstar Pink'.
2. Plants of the new Poinsettia had darker green-colored leaves than plants of 'Peterstar Pink'.
3. Plants of the new Poinsettia and 'Peterstar Pink' differed in flower bract color as plants of 'Peterstar Pink' had dark pink-colored flower bracts.

Plants of the new Poinsettia can also be compared to plants of the *Euphorbia pulcherrima* Willd. 'PER306', disclosed in U.S. Plant Pat. No. 20,398. In side-by-side comparisons conducted in Encinitas, Calif., plants of the new Poinsettia differed primarily from plants of 'PER306' in the following characteristics:

1. Plants of the new Poinsettia were not as vigorous as plants of 'PER306'.
2. Plants of the new Poinsettia had darker green-colored leaves than plants of 'PER306'.

3. Plants of the new Poinsettia flowered about three days earlier than plants of 'PER306' when grown under natural season conditions.
4. Plants of the new Poinsettia and 'PER306' differed slightly in flower bract color.

BRIEF DESCRIPTION OF THE PHOTOGRAPHS

The accompanying photographs illustrate the overall appearance of the new Poinsettia plant showing the colors as true as it is reasonably possible to obtain in colored reproductions of this type. Colors in the photographs may differ slightly from the color values cited in the detailed botanical description which accurately describe the colors of the new Poinsettia plant.

The photograph at the bottom of the sheet comprises a side perspective view of a typical flowering plant of 'PER1910' grown in a container.

The photograph at the top of the sheet is a close-up view of a typical flowering plant of 'PER1910'.

DETAILED BOTANICAL DESCRIPTION

Plants used in the aforementioned photographs and in the following detailed description were grown during the late autumn/early winter in 16.5-cm containers in a polyethylene-covered greenhouse in Encinitas, Calif. and under natural season conditions and cultural practices typical of commercial Poinsettia production. During the production of the plants, day temperatures averaged 24° C., night temperatures averaged 17° C. and light levels ranged from 3,500 to 4,500 foot-candles. Measurements and numerical values represent averages for typical flowering plants. Plants were pinched one time and were 16 weeks old when the photographs and the description were taken. In the following description, color references are made to The Royal Horticultural Society Colour Chart, 2007 Edition, except where general terms of ordinary dictionary significance are used.

Botanical classification: *Euphorbia pulcherrima* Willd. 'PER1910'.

Parentage: Naturally-occurring whole plant mutation of *Euphorbia pulcherrima* Willd. 'PER1139', disclosed in U.S. Plant Pat. No. 22,180.

Propagation:

*Type*.—Terminal vegetative cuttings.

*Time to initiate roots*.—About seven to ten days at 20° C. night temperature and 27° C. day temperature.

*Time to produce a rooted young plant*.—About four weeks at 20° C. night temperature and 27° C. day temperature.

*Root description*.—Fibrous; white in color.

Plant description:

*Plant habit and form*.—Uniform, upright and mounded plant habit; inverted triangle; large inflorescences positioned above the foliar plane; moderately vigorous growth habit.

*Plant height*.—About 32 cm.

*Plant diameter or spread*.—About 38 cm.

*Lateral branch description*.—Quantity: Freely branching habit, about seven lateral branches develop after pinching. Length: About 28 cm. Diameter: About 6.5 mm. Internode length: About 2.3 cm. Strength: Strong. Texture: Smooth, glabrous. Color: Close to 146A.

*Leaf description*.—Arrangement: Alternate, simple. Length: About 8.6 cm. Width: About 7.4 cm. Shape: Broadly lanceolate, occasionally lobed. Apex: Acuminate. Base: Rounded to somewhat attenuate. Margin: Mostly entire with random irregular pointed lobes. Aspect: Flat. Venation pattern: Pinnate, arcuate. Texture, upper surface: Sparsely pubescent; slightly rugose. Texture, lower surface: Pubescent; slightly rugose. Color: Developing leaves, upper surface: Close to N189A. Developing leaves, lower surface: Close to N138B. Fully expanded leaves, upper surface: Darker than N189A; venation, close to 146C. Fully expanded leaves, lower surface: Close to N137C; venation, close to 147D. Petiole: Length: About 7.2 cm. Diameter: About 2 mm. Texture, upper and lower surfaces: Smooth, glabrous. Color, upper and lower surfaces: Close to 146C.

Inflorescence description:

*Inflorescence type and habit*.—Terminal inflorescences are compound corymbs of cyathia with colored flower bracts subtending the cyathia; inflorescences uniformly positioned above the foliar plane.

*Fragrance*.—None detected.

*Flowering response*.—Mid-season flowering response; under natural season conditions, plants typically flower on November 23 in Southern California; under artificial long nyctoperiod/short photoperiod conditions, plants flower about 8 to 8.5 weeks later.

*Post-production longevity*.—Good post-production longevity; plants of the new Poinsettia maintain good substance and flower bract color for about four weeks under interior conditions; inflorescences persistent.

*Inflorescence diameter*.—About 28 cm.

*Inflorescence height (depth)*.—About 8.5 cm.

*Flower bracts*.—Quantity per inflorescence: About ten. Length, largest bracts: About 16.5 cm. Width, largest bracts: About 11.2 cm. Shape: Irregular, roughly elliptical occasionally lobed. Apex: Acuminate. Base: Attenuate. Margin: Entire, but irregular with random shallow pointed lobes. Texture, upper surface: Rugose, glabrous. Texture, lower surface: Rugose, slightly pubescent. Aspect: Horizontal to drooping. Venation pattern: Pinnate, arcuate. Color: Developing or transitional bracts, upper surface: Ground color, close to 18B to 18C; irregular and random splotches of close to 141A tinted with close to 51B. Developing or transitional bracts, lower surface: Close to 161C tinted with close to 146C. Fully expanded bracts, upper surface: Irregular central splotches mostly along the midvein, close to 51A; surrounded by close to 11C; venation, close to 51A and 11C; color does not change with development. Fully expanded bracts, lower surface: Irregular central splotches mostly along the midvein, close to 51C; surrounded by close to 162D; venation, close to 51C and 162D. Bract petiole: Length: About 5 cm. Diameter: About 2 mm. Texture, upper and lower surfaces: Smooth, glabrous. Color, upper and lower surfaces: Close to 182A.

*Cyathia*.—Quantity per corymb: About eight to ten. Length: About 7 mm. Width: About 7 mm. Shape: Nearly round. Texture: Somewhat rugose, glabrous. Color, immature: Close to 146A. Color, mature: Close to 146B to 146C.

*Nectaries*.—Quantity per cyathium: One to two. Length: About 4 mm. Width: About 3 mm. Shape: Roughly elliptical. Texture: Smooth, glabrous. Color: Close to 15C.

*Peduncles*.—Length: About 2 mm. Diameter: About 2 mm. Strength: Strong. Aspect: Mostly upright. Texture: Smooth, glabrous. Color: Close to 146C.

*Reproductive organs*.—Stamens and pistil development has not been observed on plants of the new Poinsettia.

*Seeds and fruits*.—Seed and fruit production have not been observed on plants of the new Poinsettia.

Disease & pest resistance: Plants of the new Poinsettia have not been shown to be resistant to pathogens and pests common to Poinsettia plants.

Temperature tolerance: Plants of the new Poinsettia have been observed to tolerate temperatures ranging from about 16° C. to about 29° C.

It is claimed:

1. A new and distinct Poinsettia plant named 'PER1910' as illustrated and described.

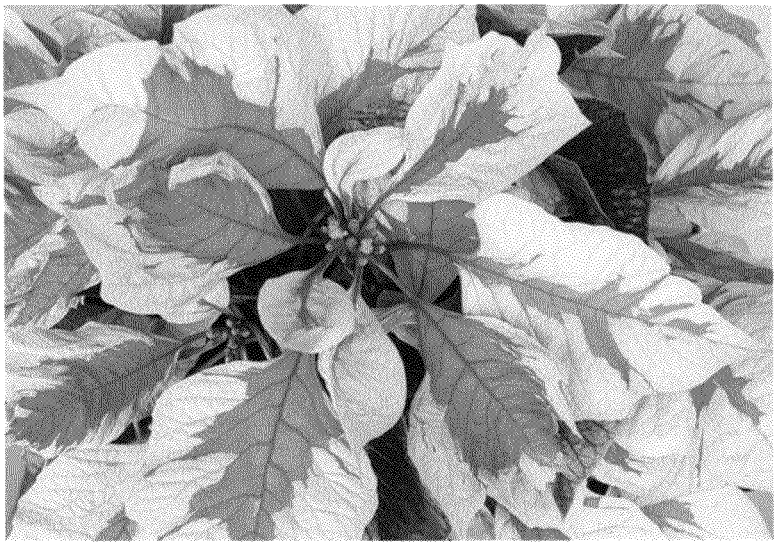
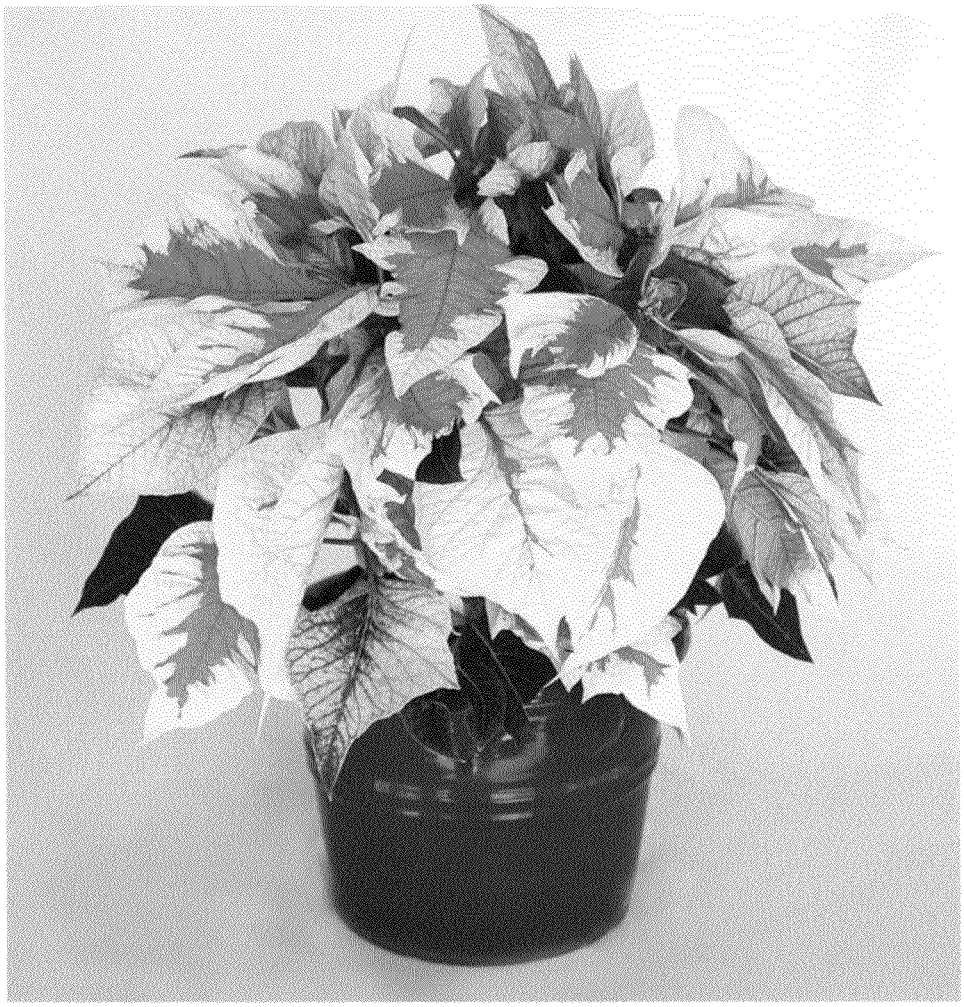

* * * * *